United States Patent
Kawakami et al.

(10) Patent No.: US 7,597,277 B2
(45) Date of Patent: Oct. 6, 2009

(54) MICROPARTICLES, MICROPARTICLE PRODUCTION METHOD, AND MICROPARTICLE PRODUCTION APPARATUS

(75) Inventors: Tomonori Kawakami, Hamamatsu (JP); Mitsuo Hiramatsu, Hamamatsu (JP); Tokio Takagi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 494 days.

(21) Appl. No.: 10/582,786

(22) PCT Filed: Dec. 14, 2004

(86) PCT No.: PCT/JP2004/018657

§ 371 (c)(1),
(2), (4) Date: Jun. 13, 2006

(87) PCT Pub. No.: WO2005/058480

PCT Pub. Date: Jun. 30, 2005

(65) Prior Publication Data

US 2007/0114306 A1    May 24, 2007

(30) Foreign Application Priority Data

Dec. 18, 2003  (JP) .............................. 2003-421509

(51) Int. Cl.
*B02C 19/18* (2006.01)
(52) U.S. Cl. ................. 241/1; 241/21; 241/301
(58) Field of Classification Search .............. 241/1, 241/2, 23, 301, 21; 264/5; 424/489
See application file for complete search history.

(56) References Cited

U.S. PATENT DOCUMENTS 5,585,044 A * 12/1996 Kawakami et al. ............. 261/1
6,431,476 B1 * 8/2002 Taylor et al. .................... 241/1

FOREIGN PATENT DOCUMENTS

JP          11-269432        10/1999

(Continued)

OTHER PUBLICATIONS

Yoshiaki Tamaki et al., "Tailoring nanoparticles of aromatic and dye molecules by excimer laser irradiation," Applied Surface Science 168 (2000) 85-88.

(Continued)

*Primary Examiner*—Jimmy T Nguyen
(74) *Attorney, Agent, or Firm*—Drinker Biddle & Reath LLP (57) ABSTRACT

A production apparatus which includes: a treatment chamber, containing a to-be-treated liquid, made up of water, which is a solvent, and raw material particles of a substance; a laser light source, illuminating laser light for microparticulation onto the to-be-treated liquid; an ultrasonic transducer, irradiating ultrasonic waves for preventing aggregation of microparticles; and a controlling device, controlling the laser light illumination by the laser light source and the ultrasonic wave irradiation by the ultrasonic transducer. A vibration amplitude of the treatment chamber is monitored by means of a microphone and a vibration amplitude measuring device to set the frequency of the ultrasonic waves to a resonance vibration frequency. A microparticle production method and production apparatus that enable substances to be microparticulated efficiently by photo-pulverization, and microparticles are thus realized.

14 Claims, 6 Drawing Sheets

FOREIGN PATENT DOCUMENTS

| | | |
|---|---|---|
| JP | 2001-113159 | 4/2001 |
| WO | WO 2004/020086 | 3/2004 |
| WO | WO 2004/080586 | 9/2004 |
| WO | WO 2005/049213 | 6/2005 |
| WO | WO 2005/058480 | 6/2005 |
| WO | WO 2005/082521 | 9/2005 |
| WO | WO 2005/092489 | 10/2005 |

OTHER PUBLICATIONS

Yoshiaki Tamaki et al., "Nanoparticle Formation of Vanadyl Phthalocyanine by Laser Ablation of Its Crystalline Powder in a Poor Solvent," J. Phys. Chem. A 2002, 106, 2135-2139.

Takeshi Sasaki et al., "Preparation of Platinum-Titanium Oxide Composite Particulate by Laser Ablation in Aqueous Solutions," The Japan Society of Applied Physics 64$^{th}$ Annual Meeting Digest (Autumn 2003, Fukuoka University), p. 1032, and its English language translation.

Bo Li et al., "Enhancement of organic nanoparticle preparation by laser ablation in aqueous solution using surfactants," Applied Surface Science 210 (2003) 171-176.

Bo Li et al., "Surfactant effects on optical absorption spectra of iron phthalocyanine nanoparticles in water," Materials Research Bulletin 39 (2004) 1265-1269.

* cited by examiner

Fig.6

MICROPARTICLES, MICROPARTICLE PRODUCTION METHOD, AND MICROPARTICLE PRODUCTION APPARATUS

TECHNICAL FIELD

The present invention relates to microparticles of an organic compound or other substance and a method and apparatus for producing microparticles.

BACKGROUND ART

Microparticulation of a substance brings about extreme increase of surface area. Microparticulation of a substance thus provides a merit that properties unique to the substance are exhibited readily. Also, in a case of a poorly soluble or insoluble substance, microparticles formed by microparticulation of the substance can be put in a state of pseudo-dissolution in a solvent such as a water (a state where the microparticles, although being suspended in the solvent, appear to be pseudo-dissolved due to the lack of light scattering).

As a conventional microparticulation method, there is known the method disclosed in Patent Document 1 (Japanese Patent Application Laid-Open No. 2001-113159). This document discloses a method of producing microparticles of organic pigments and condensed polycyclic aromatic compounds by illumination by a laser light. Microparticulation of organic compounds by laser light illumination is also described in Non-Patent Documents 1 to 3.

Patent Document 1: Japanese Patent Application Laid-Open No. 2001-113159

Non-Patent Document 1: Y Tamaki et al., "Tailoring nanoparticles of aromatic and dye molecules by excimer laser irradiation", Applied Surface Science Vol. 168, p. 85-88 (2000)

Non-Patent Document 2: Y Tamaki et al., "Nanoparticle Formation of Vanadyl Phthalocyanine by Laser Ablation of Its Crystalline Powder in a Poor Solvent", J. Phys. Chem. A 2002, 106, p. 2135-2139 (2002)

Non-Patent Document 3: B. Li et al., "Enhancement of organic nanoparticle preparation by laser ablation in aqueous solution using surfactants", Applied Surface Science Vol. 210, p. 171-176 (2003)

DISCLOSURE OF THE INVENTION

Problems to be Solved by the Invention

Employment of the above-described microparticulation arts provides possibilities of new methods of preparing raw materials, and applications are anticipated in a wide range of fields. For example, in the materials field, there are possibilities of developing new materials based on microparticles, and in the new drug development field, microparticulation opens up possibilities of enabling ADME (absorption, distribution, metabolism, and excretion) tests to be performed on new drug candidate substances that are of low solubility or are non-soluble.

Generally, microparticles of a substance have a property of aggregating in water or other solvent. Thus with microparticulation of a substance in a solvent of a to-be-treated liquid, there is an issue that a photo-pulverization action by laser light illumination and aggregation of microparticles that are formed proceed at the same time in the solvent. Such aggregated microparticles do not redisperse even upon illumination of laser light of high output and become a cause of lowering the efficiency of microparticulation by becoming scatterers of laser light.

The present invention has been made to resolve the above issue and an object thereof is to provide a microparticle production method and apparatus that enable substances to be microparticulated efficiently, and to provide microparticles.

Means for Solving the Problems

In order to achieve the above object, the present invention provides a microparticle production method of photo-pulverizing a substance in a solvent of a to-be-treated liquid to produce microparticles of the substance, the microparticle production method comprising a step of, at the same time as illuminating a laser light of a predetermined wavelength onto the to-be-treated liquid to microparticulate the substance in the solvent, irradiating ultrasonic waves onto the to-be-treated liquid to prevent aggregation of the microparticles with each other.

The present invention also provides a microparticle production apparatus that photo-pulverizes a substance in a solvent of a to-be-treated liquid to produce microparticles of the substance and includes: a treatment chamber, containing the to-be-treated liquid; a laser light source, illuminating a laser light of a predetermined wavelength, for microparticulating the substance in the solvent, onto the to-be-treated liquid contained in the treatment chamber; an ultrasonic wave irradiating means, irradiating ultrasonic waves, for preventing aggregation of the microparticles with each other, onto the to-be-treated liquid; and a controlling means, controlling the illumination of the laser light onto the to-be-treated liquid by the laser light source and the irradiation of the ultrasonic waves by the ultrasonic wave irradiating means.

With the above-described microparticle production method and apparatus, laser light illumination for microparticulation and ultrasonic wave irradiation for prevention of aggregation are carried out simultaneously on the to-be-treated liquid containing the substance to be microparticulated. Photo-pulverization by laser light illumination can thereby be performed in a state in which the progress of aggregation of the microparticles formed in the solvent is restrained. Lowering of the efficiency of microparticulation due to aggregated microparticles becoming scatterers of laser light is thus prevented and the substance can be microparticulated efficiently.

With the above-described microparticle production method and apparatus, in a case where photodegradation (photochemical reaction) of the substance is a problem, the wavelength of the laser light, illuminated from the laser light source and used to microparticulate the substance, is preferably a wavelength that is longer than the absorption band due to electronic transition of the substance. Microparticulation of the substance by laser light illumination can thereby be realized under favorable conditions that do not accompany degradation of quality.

Also with the production method, the irradiation of ultrasonic waves onto the to-be-treated liquid is preferably performed using a resonant vibration of the treatment chamber that contains the to-be-treated liquid. Likewise, with the production apparatus, the treatment chamber is preferably a chamber that enables the irradiation of ultrasonic waves onto the to-be-treated liquid using resonant vibration. Thereby, the irradiation of ultrasonic waves onto the to-be-treated liquid and the prevention of aggregation of microparticles can thus be realized favorably.

Furthermore, with the production method, a vibration amplitude of a treatment chamber that contains the to-betreated liquid is preferably monitored and a frequency of the ultrasonic waves irradiated onto the to-be-treated liquid is set based on the monitoring result. Likewise, the production apparatus preferably has a vibration amplitude monitoring means that monitors the vibration amplitude of the treatment chamber, and the controlling means preferably sets, based on the result of monitoring by the vibration amplitude monitoring means, the frequency of the ultrasonic waves irradiated onto the to-be-treated liquid. The frequency of the ultrasonic waves can thereby be set to the resonance vibration frequency in the treatment chamber or other favorable frequency, and the prevention of microparticle aggregation by ultrasonic wave irradiation can be realized reliably.

Also, with the production method, the laser light illumination and the ultrasonic wave irradiation are preferably performed while cooling the to-be-treated liquid. Likewise, the production apparatus preferably has a cooling means for performing laser light illumination and ultrasonic wave irradiation while cooling the to-be-treated liquid. The efficiency of microparticulation by laser light illumination can thereby be improved.

With the production method and apparatus, a dispersant may be added to the to-be-treated liquid. With the above-described production method and apparatus, the aggregation of microparticles can be prevented adequately even when a dispersant is added. A dispersant may also not be added. A surfactant is favorably used as a dispersant.

The substance to be microparticulated may be an organic compound. In addition to organic pigments and condensed polycyclic aromatic compounds, medicaments, etc., can be cited as examples of organic compounds. In the case of a medicament, photochemical reaction, etc., of the medicament due to laser light illumination can be prevented adequately to produce microparticles of the medicament without loss of efficacy. Also, by microparticulation of the medicament, the surface area of the medicament is increased and medicament microparticles that are improved in absorption into living tissue can be provided.

Microparticles according to the present invention are microparticles produced by the above-described microparticle production method. With such microparticles, microparticles of a substance that are produced efficiently and are in a satisfactory state can be obtained.

Effects of the Invention

With the present invention, by performing laser light illumination for microparticulation and ultrasonic wave irradiation for prevention of aggregation simultaneously on a to-be-treated liquid, a substance can be microparticulated efficiently.

DESCRIPTION OF THE SYMBOLS 1A, 1B—microparticle production apparatus, 2—to-be-treated liquid, 3—treatment chamber, 4—water (solvent), 5—raw material particle, 10—laser light source, 11—magnetic stick, 12—magnetic stirrer, 13—constant temperature device, 15—controlling device, 20, 21—ultrasonic transducer, 25, 26—ultrasonic transducer driving device, 30—microphone, 35, 36—vibration amplitude measuring device.

BEST MODES FOR CARRYING OUT THE INVENTION

Preferred embodiments of a microparticle production method, a production apparatus, and microparticles according to the present invention shall now be described in detail along with the drawings. In the description of the drawings, elements that are the same shall be provided with the same symbol and overlapping description shall be omitted. The dimensional proportions in the drawings do not necessarily match those of the description.

Figure 1:
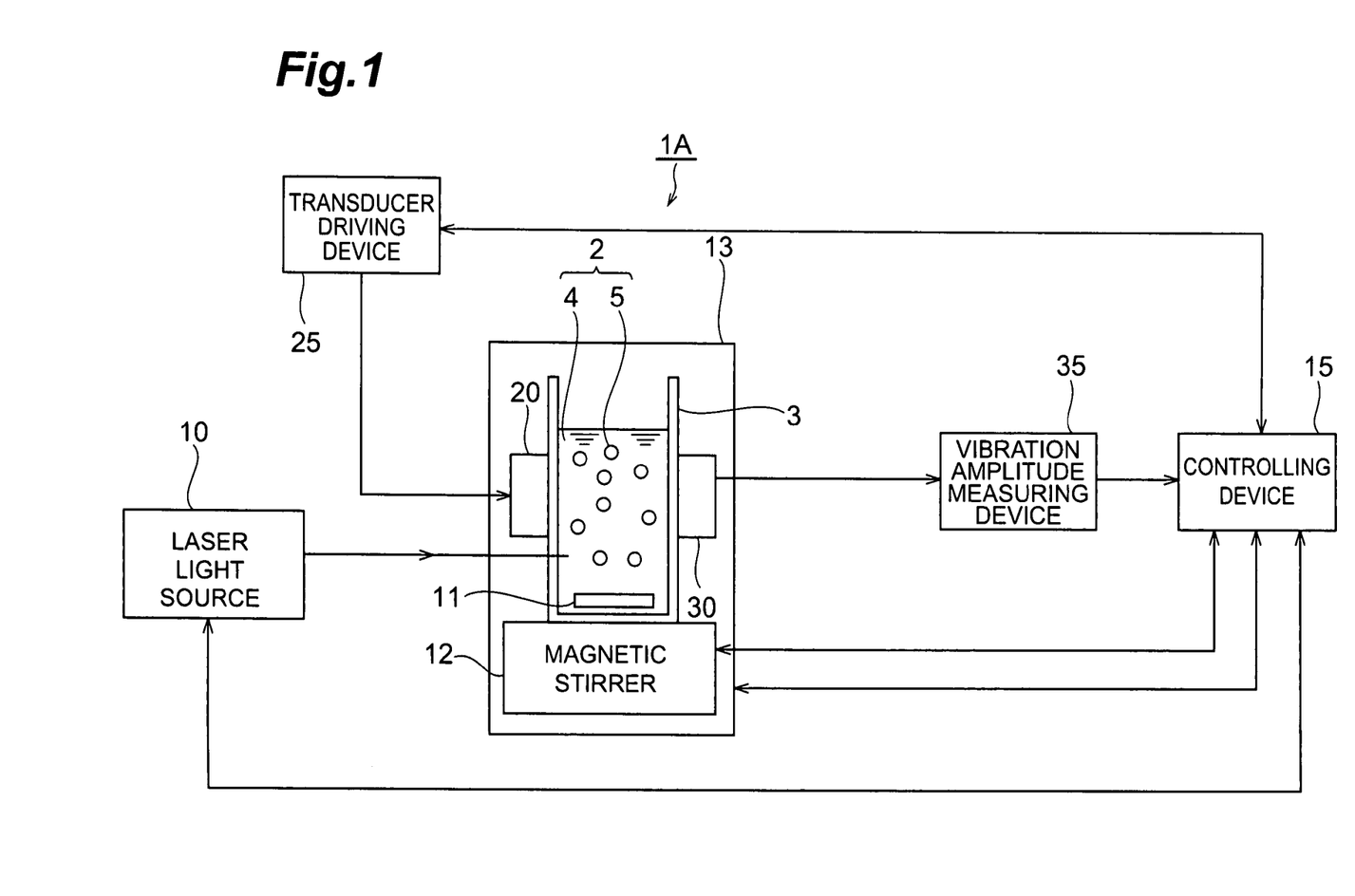
FIG. 1 is a schematic arrangement diagram of an embodiment of a microparticle production apparatus.

FIG. 1 is a schematic arrangement diagram of an embodiment of a microparticle production apparatus according to the present invention. This microparticle production apparatus 1A photo-pulverizes a substance in a solvent of a to-be-treated liquid to produce microparticles of the substance. The to-be-treated liquid 2 is made up of liquid-phase water 4, which is the solvent, and raw material particles 5 of the substance to be microparticulated, which are contained in water 4.

As shown in FIG. 1, the microparticle production apparatus 1A has a treatment chamber 3 for containing the to-be-treated liquid 2. The treatment chamber 3 is made, for example, of quartz. A constant temperature device 13 is installed on an external portion of the treatment chamber 3. The constant temperature device 13 has a function of a cooling means that cools the to-be-treated liquid 2 inside the treatment chamber 3 and also maintains the to-be-treated liquid 2, which has been cooled to a low temperature, at a constant temperature. By thus cooling the to-be-treated liquid 2, the efficiency of microparticulation can be improved. In FIG. 1, the constant temperature device 13 is illustrated schematically.

The production apparatus 1A also has a high-output laser light source 10 that illuminates a laser light of a predetermined wavelength onto the to-be-treated liquid 2, contained inside the treatment chamber 3. This laser light source 10 supplies a laser light of a wavelength favorable for microparticulating raw material particles 5 of the substance in water 4 of the to-be-treated liquid 2.

As the laser light source 10, if the wavelength to which the laser light is to be set is known in advance, a fixed-wavelength laser light source may be used. Or, a variable-wavelength laser light source may be used as the laser light source 10. In this case, laser light of an appropriate wavelength can be set and illuminated as suited according to the light absorption characteristics, etc., of the substance. Also if necessary, an attenuation filter, light attenuator, or other light intensity adjusting means may be provided for the laser light source 10.

A magnetic stick 11 is contained along with the to-be-treated liquid 2 inside the treatment chamber 3. This magnetic stick 11 and a magnetic stirrer 12 are used to disperse the raw material particles 5 in water 4 by stirring water 4 and the raw material particles 5 in the to-be-treated liquid 2 inside the treatment chamber 3.

An ultrasonic transducer 20 and an ultrasonic transducer driving device 25, which drives and controls the ultrasonic transducer 20, are installed at predetermined positions of the exterior of the treatment chamber 3. This ultrasonic transducer 20 is an ultrasonic wave irradiating means that irradiates ultrasonic waves onto the to-be-treated liquid 2 inside treatment chamber 3 to prevent microparticles from aggregating with each other. With respect to the ultrasonic transducer 20, the treatment chamber 3 is arranged so that the irradiation of ultrasonic waves onto the to-be-treated liquid 2 can be performed using resonant vibration.

In the present embodiment, the ultrasonic transducer 20 is positioned at one side face of the treatment chamber 3. A microphone 30 is mounted at a side face of the treatment chamber 3 at the side opposite the ultrasonic transducer 20. A vibration amplitude monitoring means that monitors the amplitude of vibration of the treatment chamber 3 by ultrasonic wave irradiation is arranged from the microphone 30 and a vibration amplitude measuring device 35.

The laser light source 10 and the transducer driving device 25 are connected to a controlling device 15 arranged from a computer, etc. In the present embodiment, this controlling device 15 is also connected to the magnetic stirrer 12, the constant temperature device 13, and the vibration amplitude measuring device 35. This controlling device 15 controls operations of the respective portions of the above-described production apparatus 1A to control the production of microparticles.

Next, a microparticle production method according to the present invention that makes use of the microparticle production apparatus 1A, shown in FIG. 1, shall now be described with reference to a flowchart shown in FIG. 2.

First, water 4, which is the solvent, and the raw material particles 5 of the substance to be microparticulated are mixed to prepare the to-be-treated liquid 2, and the to-be-treated liquid 2 is introduced into the treatment chamber 3 (step S101). The raw material particles 5 are put in a state of being contained in water 4 as a dissolved substance or a non-dissolved substance. The treatment chamber 3 and the to-be-treated liquid 2 inside -the treatment chamber 3 are then cooled to a predetermined low temperature by means of the constant temperature device 13 (S102). The magnetic stirrer 12 is then operated to stir the to-be-treated liquid 2 by means of the magnetic stick 11 and disperse the raw material particles 5 in water 4 (S103).

The frequency of the ultrasonic waves to be irradiated onto the to-be-treated liquid 2 is then set (S104). First, in the state in which cooling by the constant temperature device 13 and stirring by the magnetic stick 11 are being performed as described above, the ultrasonic transducer 20 is driven by means of the transducer driving device 25 to irradiate ultrasonic waves onto the treatment chamber 3 and the to-be-treated liquid 2. The amplitude of vibration of the treatment chamber 3 by the ultrasonic wave irradiation is monitored by the microphone 30 and an electrical signal indicating the monitoring result is outputted to the controlling device 15 through the vibration amplitude measuring device 35.

The controlling device 15 references information concerning the frequency of ultrasonic waves from the transducer driving device 25 and information on the monitoring results from the vibration amplitude measuring device 35 and determines a relationship between the vibration frequency of the irradiated ultrasonic waves and the vibration amplitude (vibration intensity) of the treatment chamber 3. Then, based on the relationship between the vibration frequency and amplitude, the controlling device 15 sets the frequency of ultrasonic waves irradiated onto the to-be-treated liquid 2. Specifically, because in the frequency and amplitude relationship that is determined, the frequency at which the vibration amplitude is the maximum is the resonance vibration frequency in the treatment chamber 3, the frequency of ultrasonic waves irradiated from the ultrasonic transducer 20 onto the treatment chamber 3 is set, through the transducer driving device 25, to the resonance vibration frequency.

The laser light source 10 is then controlled by the controlling device 15, and the laser light, with the wavelength set according to the light absorption characteristics of the substance making up the raw material particles 5, etc., is illuminated from the laser light source 10 onto the to-be-treated liquid 2. By this laser light illumination, the raw material particles 5 in water 4 in the to-be-treated liquid 2 inside the treatment chamber 3 are microparticulated and microparticles of the substance are produced. Here, irradiation of ultrasonic waves onto the treatment chamber 3 and the to-be-treated liquid 2 by the ultrasonic transducer 20 is performed at the same time as the illumination of laser light. By this ultrasonic wave irradiation, the mutual aggregation of the microparticles of the substance that are formed in water 4 is prevented (S105).

The state of progress of microparticulation in the to-be-treated liquid 2 is then checked (S106). If the state of progress does not meet a certain condition of completion of microparticulation, the microparticulation process is continued further. On the other hand, if the state of progress meets the condition of completion of microparticulation and it is judged that the substance is microparticulated in the entirety of the to-be-treated liquid 2, the laser light illumination and the ultrasonic wave irradiation are stopped (S107), and the microparticulation of the substance is ended.

Effects of the microparticle production method and production apparatus according to the present embodiment shall now be described.

Figure 2:
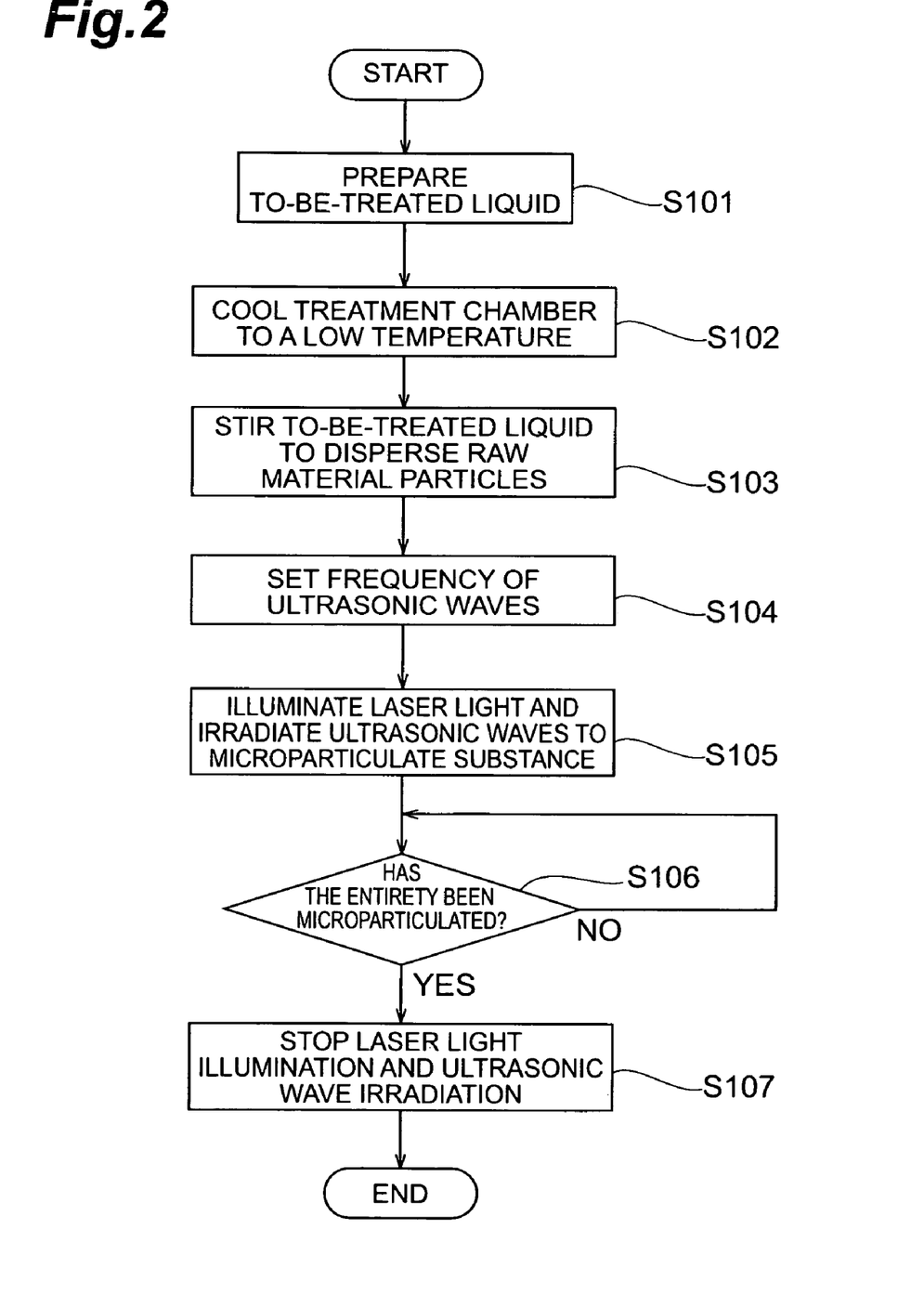
FIG. 2 is a flowchart of an example of a microparticle production method using the production apparatus shown in FIG. 1.

With the microparticle production method and apparatus shown in FIGS. 1 and 2, laser light illumination by the laser light source 10 for microparticulation and ultrasonic wave irradiation by the ultrasonic transducer 20 for prevention of aggregation are carried out simultaneously on the to-be-treated liquid 2 containing the raw material particles 5 of the substance to be microparticulated. Photo-pulverization by laser light illumination can thereby be performed in a state in which the progress of aggregation of the microparticles formed in water 4, which is the solvent, is restrained.

That is, by irradiating ultrasonic waves onto the to-be-treated liquid 2, primary microparticles, which are the smallest masses, can be prevented from aggregating and aggregated masses can be redispersed immediately after aggregation. Thus by combining ultrasonic wave irradiation with laser light illumination, the formation of aggregated microparticles by mutual aggregation of microparticles formed in the to-be-treated liquid 2 can be restrained effectively. By such prevention of aggregation of the microparticles, lowering of the efficiency of microparticulation due to aggregated microparticles becoming scatterers of laser light is prevented. The substance can thus be microparticulated efficiently. Also by using the above-described production method and apparatus, microparticles of a substance that are produced efficiently and are in a satisfactory state can be obtained.

Such a microparticle production method and apparatus that make combined use of ultrasonic wave irradiation are especially effective for performing microparticulation of a substance efficiently by making the concentration of microparticles high. That is, there are cases where, to improve the efficiency of microparticulation by laser light illumination, the microparticulation must be carried out with the concentration of the microparticles formed in the solvent being made high. However, when microparticles are present at a high concentration, the conditions tend to cause mutual aggregation of the microparticles readily. The efficiency of microparticulation is thus lowered by the scattering of the laser light by the aggregated microparticles or the formed microparticles become large in fluctuation of particle size and thus poor in quality. In contrast, by performing ultrasonic wave irradiation at the same time as laser light illumination as described above, microparticulation of the substance can be performed under good conditions even when microparticles are present at a high concentration.

Here, satisfactory primary microparticles can be formed efficiently without the addition of a surfactant or with the addition of a surfactant at a low concentration to the to-be-treated liquid 2. If a surfactant is to be added to the to-be-treated liquid 2, it is preferably added at a concentration no more than a critical micelle concentration. With the method described above, the aggregation of microparticles can be prevented adequately under the condition of adding a surfactant at a low concentration or under the condition of not adding a surfactant. In general with the above-described method and apparatus, a dispersant may be added to the to-be-treated liquid, and the aggregation of microparticles can be prevented adequately even under such conditions. In this case, the above-described surfactant is favorably used as the dispersant.

With the production apparatus 1A shown in FIG. 1, ultrasonic wave irradiation by the ultrasonic transducer 20 is performed while making use of the resonant vibration of the treatment chamber 3 that contains the to-be-treated liquid 2. The prevention of aggregation of microparticles by irradiation of ultrasonic waves onto the to-be-treated liquid 2 can thus be realized favorably. As the treatment chamber 3, for example, a chamber with the shape of a rectangular column, a cylinder, or a sphere, with which resonant vibration can be realized, is preferably used. Also, although when using resonant vibration, durability of the treatment chamber 3 against resonant vibration of large vibration is required, the durability can be improved by using a cylindrical or spherical chamber and thereby lessening joint portions that are weak to vibration.

Furthermore with the production apparatus 1A, the vibration amplitude of the treatment chamber 3 is monitored by means of the microphone 30 and the vibration amplitude measuring device 35 and the ultrasonic wave frequency is set based on the monitoring result. The ultrasonic wave frequency can thus be set to the resonance vibration frequency of treatment chamber 3 or other favorable frequency, and the prevention of microparticle aggregation by ultrasonic wave irradiation can be realized reliably. Any of various means besides the microphone 30 may be used as the vibration amplitude monitoring means.

In regard to the aggregation of microparticles in the solvent, the lower the solubility of the microparticles, the stronger the aggregation property, and the effect of aggregation prevention by combined use of ultrasonic wave irradiation is especially high in such a case. Also with the above-described embodiment, laser light illumination and ultrasonic wave irradiation are performed while cooling the to-be-treated liquid 2 by means of the constant temperature device 13. Such lowering of the temperature of the solvent is effective in terms of improving the efficiency of microparticulation by laser light illumination and also contributes to the lowering of aggregation forces of the microparticles, the forming of a strong resonant vibration field, etc.

Here, the wavelength of the laser light illuminated onto the to-be-treated liquid 2 from the laser light source 10 is preferably a wavelength that is longer than the absorption band due to electronic transition of the substance to be microparticulated. Also in a case of a substance, with which photodegradation (photochemical reaction) must be avoided, the wavelength is preferably a wavelength in the infrared range and more preferably a wavelength of no less than 900 nm. Microparticulation of the substance by laser light illumination can thereby be realized under favorable conditions that do not accompany degradation of quality. Also a pulse laser light source is preferably used as the laser light source 10. In particular, to perform microparticulation at an adequate efficiency while restraining the occurrence of unwanted photochemical reactions and thermal decomposition in the to-be-treated liquid 2, a pulse laser light source, which, as long as the threshold of the light intensity that causes photo-pulverization is exceeded, is low in illumination energy per pulse and has a high repetition frequency, is preferably used.

Also, the substance of the raw material particles 5 to be microparticulated by laser light illumination combined with ultrasonic wave irradiation may be an organic compound. Examples of organic compounds include, for example, organic pigments, condensed polycyclic aromatic compounds, medicaments (medicinal agents, medical product related substances), etc. In the case of a medicament, photochemical reaction, etc., of the medicament due to laser light illumination can be prevented adequately by performing microparticulation efficiently. Microparticles of the medicament can thereby be produced without loss of efficacy. Also in regard to photochemical reactions, the occurrence of photochemical reactions can be restrained further by favorable selection of the wavelength of the laser light (for example, selection of the above-described wavelength of no less than 900 nm) illuminated onto the to-be-treated liquid 2.

To be more detailed, in many cases, an organic compound that is used as a medicament contains comparatively weak chemical bonds in the molecular structure, and when ultraviolet light or other light is illuminated onto such an organic compound, although microparticles can be formed in part, photochemical reactions of the organic compound via electron excitation states may occur in part at the same time and form impurities. Especially in a case where the organic compound is a medicament (medical product) that is administered into a body, such circumstances must be avoided as much as possible because the impurities may cause side effects and have ill effects on a living body. In contrast, by producing microparticles of the organic compound by the above-described production method that enables the occurrence of photochemical reactions to be restrained, the forming of impurities can be restrained adequately.

Also by realizing microparticulation of medicaments while maintaining the efficacy as described above, physicochemical research, screening, and other processes of examining and determining candidate compounds, ADME tests, general toxicity, general pharmacology, efficacy, and biochemistry research in preclinical tests using animals, and clinical tests, which could not be conducted with the medicament being in a form prior to microparticulation, are made possible. Also, because by the above-described production method, an extremely wide variety of medicaments that can be administered to living bodies can be obtained, the width of selection of medicaments can be broadened significantly. Also, since by microparticulation of a medicament, the medicament is increased in surface area and improved in absorption into living tissue, medicament microparticles that are effective in small amounts can be obtained. Such a microparticulation process is also effective for organic compounds besides medicaments.

Specific examples of organic compounds to be microparticulated include clobetasone butyrate, carbamazepine, and other poorly soluble medicaments. Besides the above-described medical drug substances, the above-described microparticle production method and apparatus can also be applied to medical drug candidate substances (natural substances, compound libraries, etc.), quasi-drugs, cosmetics, etc.

As the solvent of the medicament or other organic compound, water is preferably used as described above, and small amounts of alcohol, sugar, or salt may be contained. Or, a solvent besides water may be used. Examples of such a solvent include ethyl alcohol, which is a monohydric alcohol, glycols (propylene glycol, polyethylene glycol, etc.), which are dihydric alcohols, glycerol, which is a trihydric alcohol, etc. Soybean oil, corn oil, sesame oil, peanut oil, etc., which are vegetable oils, may also be used as the solvent. In a case of use as an injectable solution, such a solvent can be used favorably as an organic solvent of a non-aqueous injectable solution.

With the production method according to the present embodiment, microparticulation is enabled without the addition of a surfactant or with the addition of a surfactant at a low concentration as described above. This presents a large merit in applications to medical products, with which the types and concentrations of additives are restricted strictly.

In regard to the stoppage of laser light illumination and ultrasonic wave irradiation onto the to-be-treated liquid 2 in the production of microparticles by the microparticle production apparatus 1A shown in FIG. 1, the intensity and duration of the laser light necessary for microparticulation can be determined in advance and the laser light illumination can be controlled based on the treatment time. Or, a monitoring means that monitors the microparticulation state of the raw material particles 5 in the to-be-treated liquid 2 may be installed and the laser light illumination may be controlled according to the monitoring result.

Figure 3:
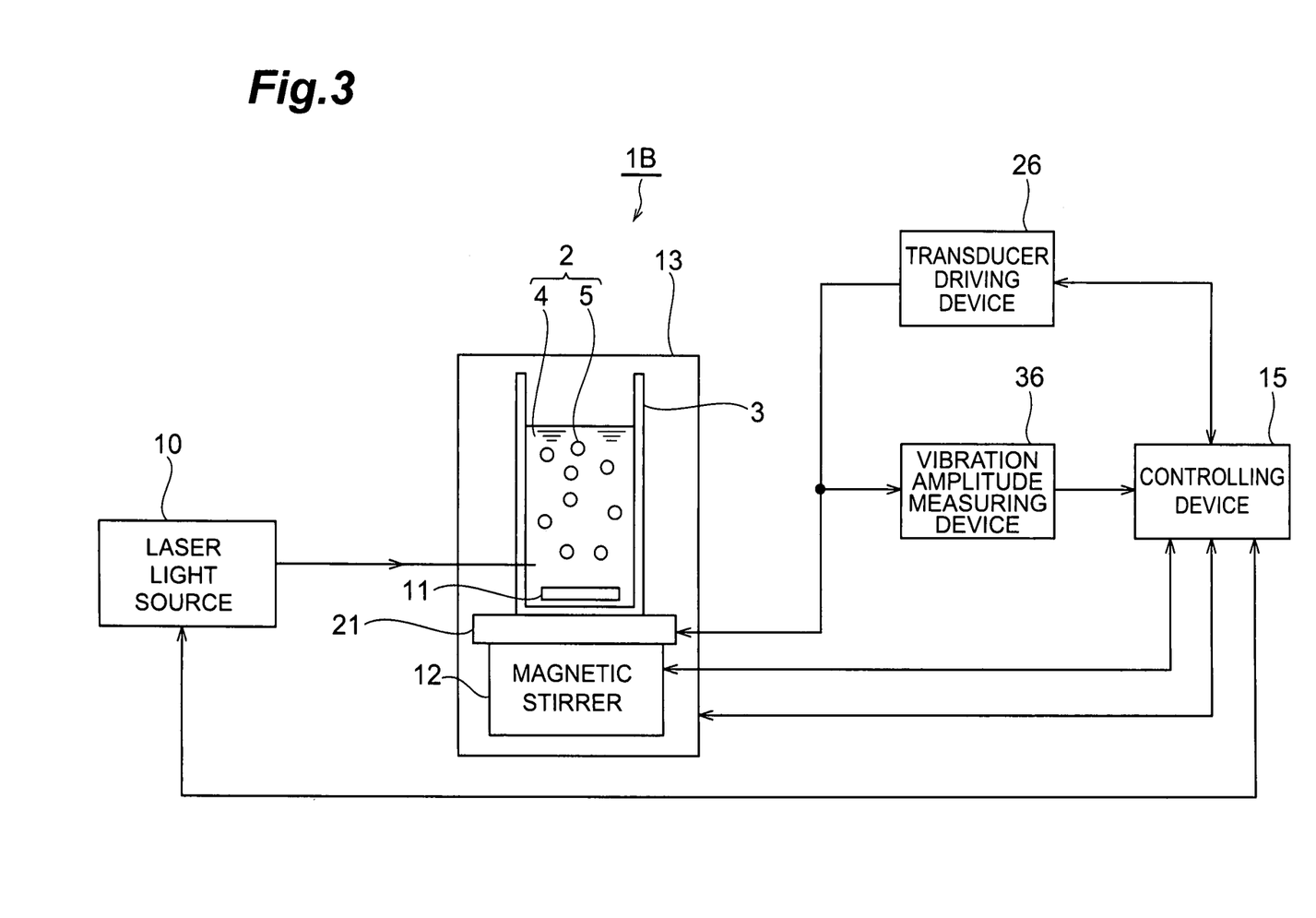
FIG. 3 is a schematic arrangement diagram of another embodiment of a microparticle production apparatus.

FIG. 3 is a schematic arrangement diagram of another embodiment of a microparticle production apparatus according to the present invention. In this microparticle production apparatus 1B, the arrangements of the treatment chamber 3, which contains the to-be-treated liquid 2 made up of water 4 and the raw material particles 5 of a substance, the laser light source 10, the magnetic stick 11, the magnetic stirrer 12, the constant temperature device 13, and the controlling device 15 are the same as those of production apparatus 1A shown in FIG. 1.

In the present embodiment an ultrasonic transducer 21, which is an ultrasonic wave irradiating means, is positioned at a bottom face side of the treatment chamber 3. Also, an ultrasonic transducer driving device 26 that drives and controls the ultrasonic transducer 21 is installed. Furthermore, a signal from the transducer driving device 26 is also inputted into a vibration amplitude measuring device 36. The vibration amplitude measuring device 36 measures the vibration amplitude of the treatment chamber 3 by the signal from the transducer driving device 26. In the present embodiment, a vibration amplitude monitoring means that monitors the vibration amplitude of the treatment chamber 3 by ultrasonic wave irradiation is arranged from the ultrasonic transducer 21, the transducer driving device 26, and the vibration amplitude measuring device 36.

In such an arrangement in which the ultrasonic transducer 21 is installed at the bottom face of the treatment chamber 3, resonant vibration occurs between the bottom surface and upper surface of water 4. When the resonant vibration state is attained, the ultrasonic transducer 21 vibrates greatly and the voltage applied to the transducer becomes large. Thus by monitoring the amplitude variation of the voltage applied to the ultrasonic transducer 21 by the vibration amplitude measuring device 36, the resonance vibration frequency of the ultrasonic wave irradiation is obtained. This arrangement provides a merit that a microphone 30 or other device for monitoring the vibration amplitude does not have to be installed separately as shown in FIG. 1.

Although details of the present invention shall now be described more specifically by way of examples, the present invention is not restricted to the following examples.

EXAMPLE 1

In this example, microparticulation was attempted with the pigment, VOPc (oxovanadium phthalocyanine), as the substance of the raw material particles 5 to be microparticulated. The VOPc is a pigment extremely close to being insoluble in water and exhibits a strongly aggregating property in water when microparticulated. First, six samples, with each of which 3 ml of a highly concentrated suspension, containing the VOPc raw material particles of 10 to 70 μm particle diameter at a concentration of 1 mg/ml, are placed in a quartz square cell of a treatment chamber 3, were prepared. As each quartz square cell, that of dimensions, 10 mm×10 mm×40 mm, was used and at the bottom face of each cell, a piezo transducer of φ16 mm diameter and 3 mm thickness was attached as the ultrasonic transducer 21 (see FIG. 3).

The above-described six samples were respectively subject to the different treatments of (1) leaving the raw material particles as they are; (2) performing just an ultrasonic treatment; (3) performing just an ultrasonic resonance treatment; (4) performing just a photo-pulverization treatment; (5) performing the ultrasonic treatment and the photo-pulverization treatment simultaneously; and (6) performing the ultrasonic resonance treatment and the photo-pulverization treatment simultaneously. The effects of variation of the particle diameter of the VOPc by the respective treatments were then examined using a particle size distribution measuring device (SALD7000, made by Shimadzu Corp.). All of these samples did not contain a surfactant for preventing the aggregation of microparticles and were in a state in which aggregated microparticles form readily.

Among the respective treatments described above, in the "ultrasonic treatment," the ultrasonic transducer is operated at 30 kHz, which is not a resonance vibration frequency, to perform treatment for 30 minutes. In the "ultrasonic resonance treatment," the ultrasonic transducer is operated at a resonance vibration frequency of 51 kHz to perform treatment for 30 minutes. The conditions of laser light illumination in the photo-pulverization treatment are: a wavelength of 1064 nm; a light intensity per pulse of pulse laser light of 688 mJ/cm$^2$, a laser light spot diameter of φ5 mm (illumination area of 0.196 cm$^2$), a repetition frequency of 10 Hz, a pulse width FWHM of 4 ns, and an illumination duration of 30 minutes. In this Example, as a pretreatment for determining the particle diameter distribution by the particle size distribution measuring device, 100 μl of a surfactant (Nonidet P-40; trade name: Igapal CA-630; molecular weight: 602; critical micelle concentration: 0.29 mM) were added to 3ml of the to-be-treated liquid, and the particle diameter distribution was measured under conditions in which re-aggregation of particles was restrained. The water temperature during measurement was set to the room temperature of 25° C.

Figure 4:
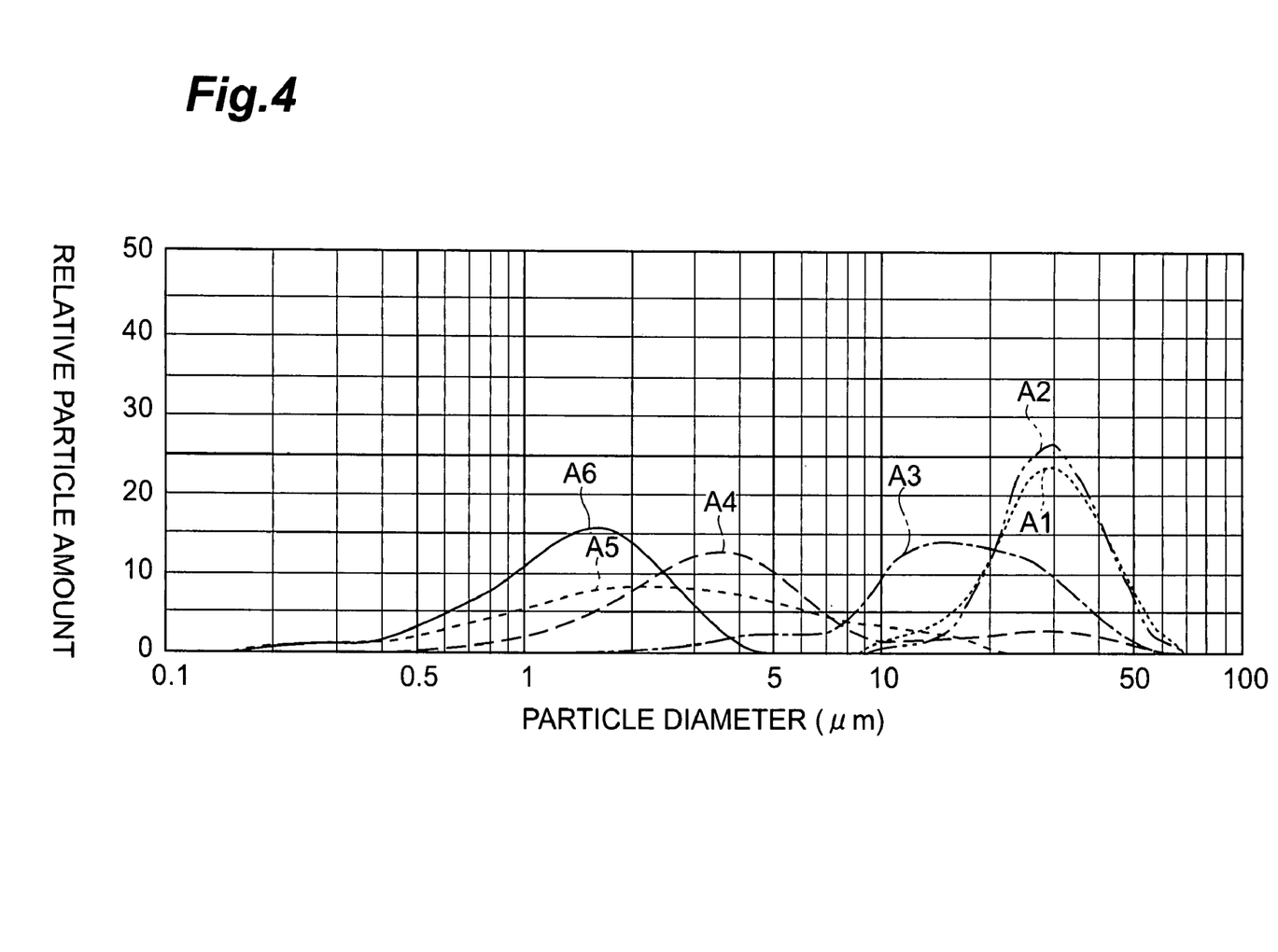
FIG. 4 shows graphs of particle diameter distributions of VOPc microparticles.

FIG. 4 shows graphs of particle diameter distributions of the VOPc microparticles subject to the respective treatments described above. With these graphs, the abscissa indicates the particle diameter (μm) of the VOPc and the ordinate indicates the relative particle amount in terms of volume. Graphs A1 to A6 correspond to treatments (1) to (6), respectively.

A comparison of graphs A1 and A2 of FIG. 4 shows that the particle diameter distribution of the VOPc is not changed by just the ultrasonic treatment. A comparison of graphs A2 and A3 shows that with graph A3, corresponding to the ultrasonic resonance treatment, slight microparticulation is seen due to large vibrations acting on the particles.

From a comparison of graph A4, corresponding to the case of performing just the photo-pulverization by laser light illumination, and graphs A5 and A6, corresponding to the cases of performing the ultrasonic treatment and the ultrasonic resonance treatment, respectively, at the same time as the photo-pulverization treatment, it can be confirmed that the efficiency of microparticulation is improved by the combined use of ultrasonic wave irradiation with laser light illumination. Graph A6, corresponding to the case of using ultrasonic wave irradiation by resonant vibration, shows that in this case, the action of redispersing aggregated microparticles is strong due to the vibration amplitude being large in comparison to normal ultrasonic wave irradiation and that as a result, scattering loss of the laser light by aggregated microparticles is lessened and the efficiency of microparticulation is made especially high. It is thus confirmed that when photo-pulverization is to be performed in a state in which the aggregation of microparticles occurs readily, the combined use of ultrasonic wave irradiation with laser light illumination is effective for improving the microparticulation efficiency.

EXAMPLE 2

As in Example 1, microparticulation was attempted with the pigment, VOPc, as the substance of the raw material particles 5 to be microparticulated in this Example. However, here, a surfactant (the above-described P-40) was added to a concentration of 0.1 mM to set conditions in which the aggregation of microparticles is slightly restrained. In such a case where a surfactant is added, due to the lowness of aggregation, adequate redispersion of aggregated microparticles is possible even with ultrasonic wave irradiation that is not a resonant vibration. Thus in this Example, ultrasonic resonance treatment was not performed, and samples were respectively subject to the five different treatments of (1) leaving the raw material particles as they are; (2) performing just an ultrasonic treatment; (3) performing just a photo-pulverization treatment; (4) performing the ultrasonic treatment and the photo-pulverization treatment simultaneously; and (5) performing the photo-pulverization treatment upon adding the surfactant to a high concentration (10 mM) (Comparative Example). The conditions of the ultrasonic treatment and the photo-pulverization treatment are the same as those of Example 1.

Figure 5:
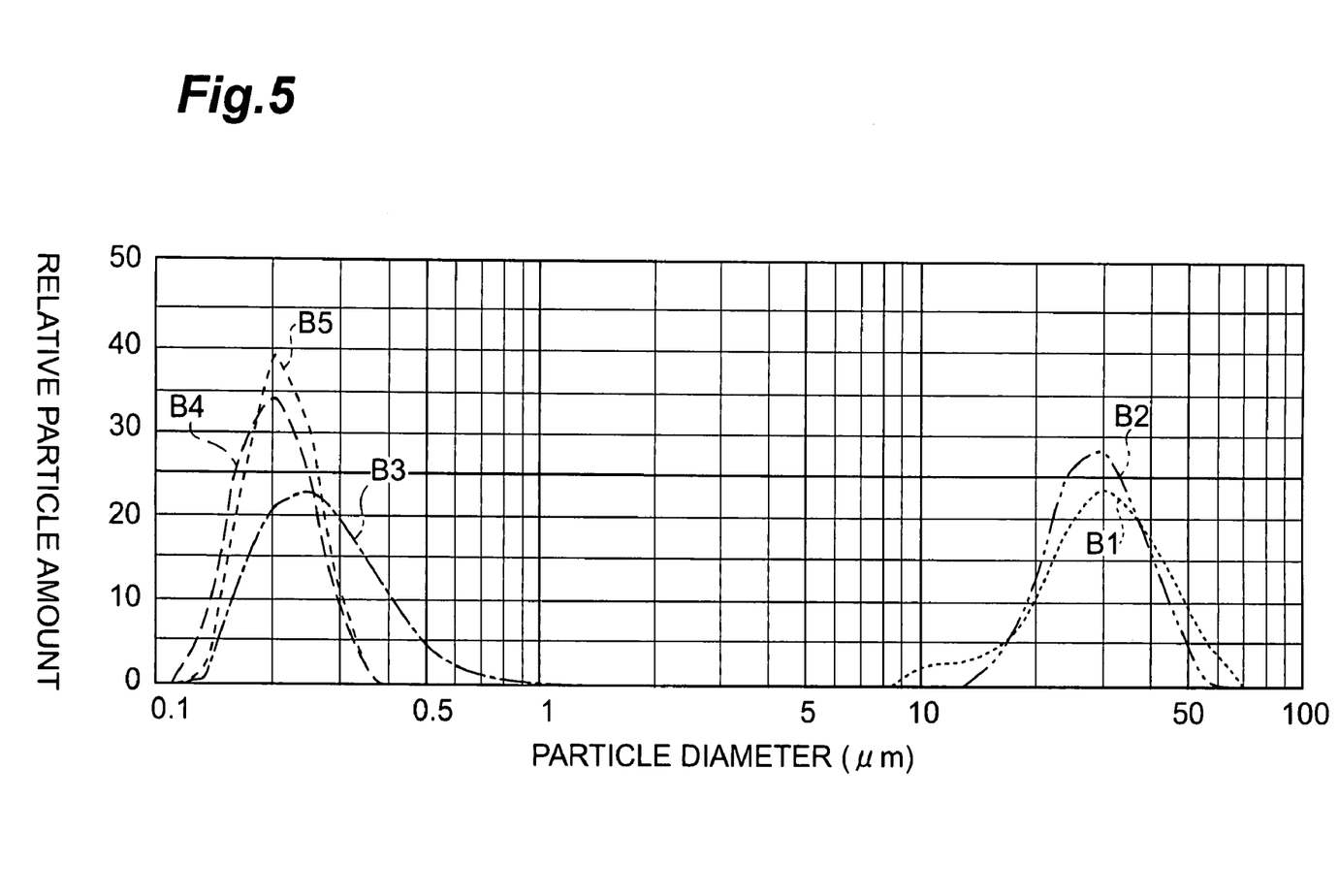
FIG. 5 shows graphs of particle diameter distributions of VOPc microparticles under the presence of a surfactant.

FIG. 5 shows graphs of particle diameter distributions of the VOPc microparticles subject to the respective treatments described above. With these graphs, the abscissa indicates the particle diameter (μm) of the VOPc and the ordinate indicates the relative particle amount in terms of volume. Graphs B1 to B5 correspond to treatments (1) to (5), respectively.

A comparison of graphs B1 and B2 of FIG. 5 shows that the particle diameter distribution of the VOPc is not changed by just the ultrasonic treatment. Graph B3, corresponding to the photo-pulverization treatment by laser light illumination, shows that although the particle diameters of the microparticles are lowered significantly, the distribution spreads in the large diameter direction. Comparison of this graph B3, with graph B4, corresponding to the case of performing the ultrasonic treatment at the same time as the photo-pulverization treatment, it can be confirmed that the efficiency of microparticulation is improved by the combined use of ultrasonic wave irradiation with laser light illumination.

Although graph B5, for the case of adding the surfactant to a high concentration, shows that photo-pulverization is carried out under conditions in which microparticles do not aggregate, substantially the same particle diameter distribution as that of graph B5 was obtained in the above-described case of graph B4. It is thus confirmed that even under conditions where slight aggregation of microparticles occur, the combined use of ultrasonic wave irradiation with laser light illumination creates a state where there are no aggregated microparticles and can realize photo-pulverization equivalent to the case of adding a surfactant to a high concentration.

EXAMPLE 3

In this Example, microparticulation was attempted with the poorly soluble medicament, clobetasone butyrate (a synthetic topical corticosteroid), as the substance of the raw material particles 5 to be microparticulated. First, samples were prepared by suspending clobetasone butyrate at a concentration of 0.5 mg/ml in 3ml of water and then adding a surfactant (Tween 80; molecular weight: 1310; critical micelle concentration: 0.012 mM) to a concentration 0.0054 mM. The quartz square cells, etc., used are the same as those used in Example 1.

The above-described samples were respectively subject to the different treatments of (1) leaving the raw material particles as they were; (2) performing just an ultrasonic resonance treatment; (3) performing just a photo-pulverization treatment; (4) performing the photo-pulverization treatment after performing the ultrasonic resonance treatment; and (5) performing the ultrasonic resonance treatment and the photo-pulverization treatment simultaneously. The effects of variation of the particle diameter of clobetasone butyrate by the respective treatments were then examined using the particle size distribution measuring device.

Among the respective treatments described above, in the "ultrasonic resonance treatment," the ultrasonic transducer is operated at the resonance vibration frequency of 51 kHz to perform treatment for 30 minutes. The conditions of laser light illumination in the photo-pulverization treatment are: a wavelength of 1064 nm; a light intensity per pulse of pulse laser light of 2667 mJ/cm$^2$, a laser light spot diameter of φ3 mm (illumination area of 0.07 cm$^2$), a repetition frequency of 10 Hz, a pulse width FWHM of 4 ns, and an illumination duration of 30 minutes.

Figure 6:
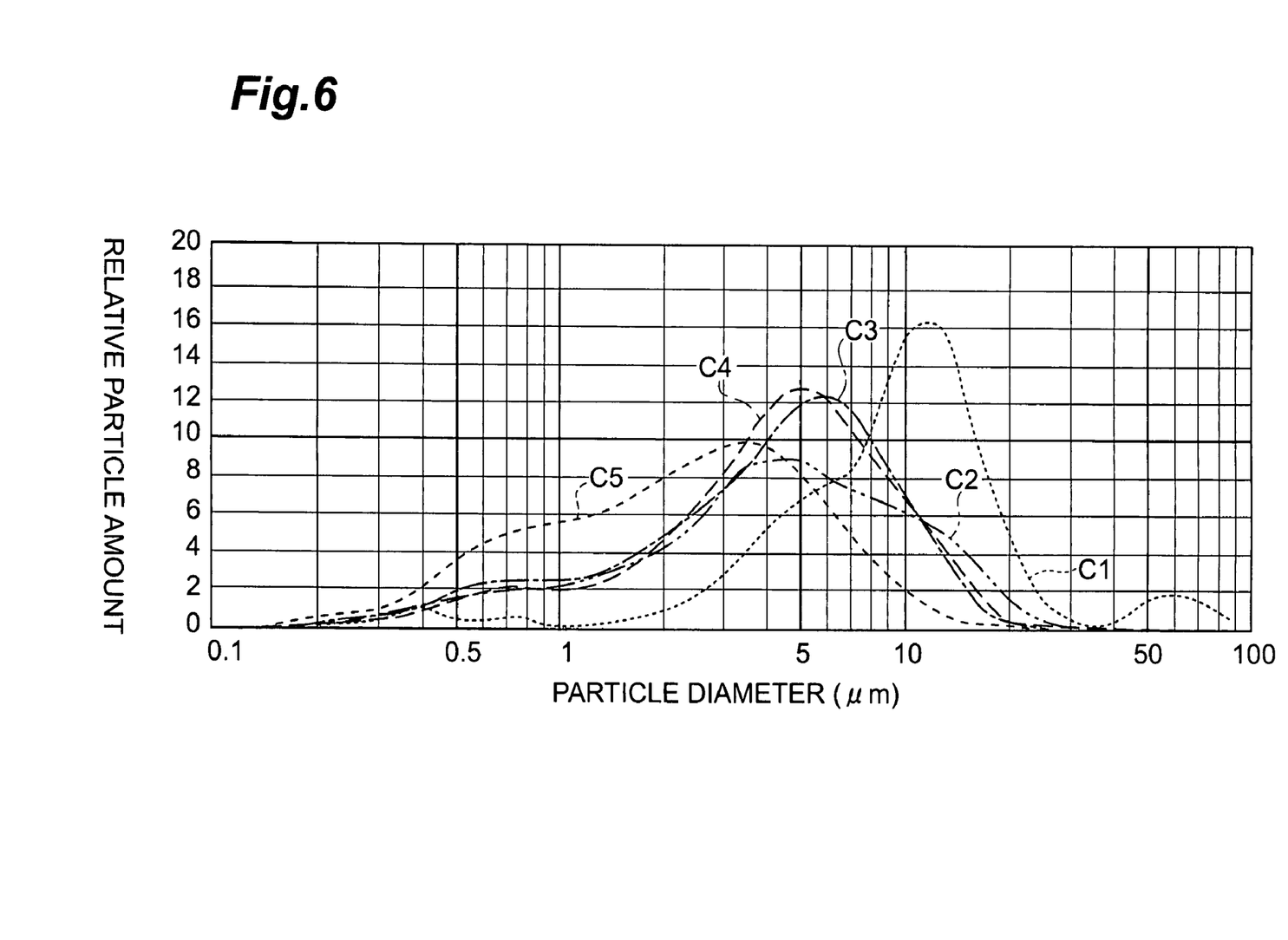
FIG. 6 shows graphs of particle diameter distributions of clobetasone butyrate.

FIG. 6 shows graphs of particle diameter distributions of clobetasone butyrate subject to the respective treatments described above. With these graphs, the abscissa indicates the particle diameter (μm) of clobetasone butyrate and the ordinate indicates the relative particle amount in terms of volume. Graphs C1 to C5 correspond to treatments (1) to (5), respectively.

A comparison of graphs C1 and C2 of FIG. 6 shows that in the case of graph C2, corresponding to the ultrasonic resonance treatment, microparticulation has occurred slightly. A comparison of graph C3, corresponding to the case of performing just the photo-pulverization by laser light illumination, and graph C4, corresponding to the case of performing the photo-pulverization treatment after the ultrasonic resonance treatment, shows that the particle diameter distribution does not change much even if the ultrasonic resonance treatment and the photo-pulverization treatment are carried out successively.

On the other hand, from a comparison of these graphs C3 and C4 with graph C5, corresponding to the case of performing the ultrasonic resonance treatment at the same time as the photo-pulverization treatment, it can be confirmed that microparticulation progresses further and the efficiency of microparticulation is improved by the combined use of ultrasonic wave irradiation with laser light illumination. This is the result of photo-pulverization by laser light illumination being carried out satisfactorily due to redispersion of aggregated microparticles by ultrasonic wave irradiation and the consequent reduction of scattering loss of the laser light by aggregated microparticles. It is thus confirmed that even in a case of microparticulating a medicament (medical product) as an organic compound to be microparticulated, if photo-pulverization in a state in which the aggregation of microparticles occurs readily is to be performed, the combined use of ultrasonic wave irradiation with laser light illumination is effective for improving the microparticulation efficiency.

The microparticle production method and production apparatus and the microparticles according to the present invention are not restricted to the above-described embodiments and examples, and various modifications are possible. For example, although it is preferable to perform laser light illumination and ultrasonic wave irradiation simultaneously, laser light illumination and ultrasonic wave irradiation may be performed alternatingly within a short time in which primary microparticles do not aggregate to provide effects equivalent to applying the two simultaneously. Also, the material of the treatment chamber 3 used in the production apparatus is not restricted to quartz, and various materials may be used in consideration of the laser light transmission characteristics, characteristics of resonant vibration with respect to ultrasonic waves, etc. Also in regard to the ultrasonic wave irradiating means, the vibration amplitude monitoring means, etc., for the to-be-treated liquid 2, arrangements besides the above may be used. The vibration amplitude monitoring means does not have to be provided if it is not required. In regard to the frequency of ultrasonic waves to be irradiated onto the to-be-treated liquid 2, a frequency besides a resonance vibration frequency may be set.

INDUSTRIAL APPLICABILITY

The present invention can be used to provide a microparticle production method and production apparatus that enable substances to be microparticulated efficiently, and to provide microparticles.

The invention claimed is:

1. A microparticle production method of photo-pulverizing a substance in a solvent of a to-be-treated liquid to produce microparticles of the substance,
the microparticle production method comprising a step of illuminating a laser light of a predetermined wavelength onto the to-be-treated liquid to microparticulate the substance in the solvent at the same time as irradiating ultrasonic waves onto the to-be-treated liquid to prevent aggregation of the microparticles with each other.

2. The production method according to claim 1, wherein the wavelength of the laser light used for microparticulation of the substance is longer than the wavelength of a absorption band due to electronic transition of the substance.

3. The production method according to claim 1, wherein the irradiation of the ultrasonic waves onto the to-be-treated liquid is performed using a resonant vibration of a treatment chamber that contains the to-be-treated liquid.

4. The production method according to claim 1, wherein a vibration amplitude of a treatment chamber that contains the to-be-treated liquid is monitored and a frequency of the ultrasonic waves irradiated onto the to-be-treated liquid is set based on the monitoring result.

5. The production method according to claim 1, wherein the laser light illumination and the ultrasonic wave irradiation are performed while cooling the to-be-treated liquid.

6. The production method according to claim 1, wherein a dispersant is added to the to-be-treated liquid.

7. The production method according to claim 1, wherein the substance is an organic compound.

8. A microparticle production apparatus that photo-pulverizes a substance in a solvent of a to-be-treated liquid to produce microparticles of the substance, the microparticle production apparatus comprising:
a treatment chamber, containing the to-be-treated liquid;
a laser light source, illuminating a laser light of a predetermined wavelength, for microparticulating the substance in the solvent, onto the to-be-treated liquid contained in the treatment chamber;
an ultrasonic wave irradiating means, irradiating ultrasonic waves, for preventing aggregation of the microparticles with each other, onto the to-be-treated liquid; and
a controlling means, said controlling means is configured to illuminate the laser light onto the to-be-treated liquid by the laser light source at the same time as irradiating the ultrasonic waves by the ultrasonic wave irradiating means onto the to-be treated liquid.

9. The production apparatus according to claim 8, wherein the wavelength of the laser light illuminated from the laser light source is longer than the wavelength of a absorption band due to electronic transition of the substance.

10. The production apparatus according to claim 8, wherein the treatment chamber is a chamber enabling the irradiation of the ultrasonic waves onto the to-be-treated liquid to be performed using a resonant vibration.

11. The production apparatus according to claim 8, further comprising:
a vibration amplitude monitoring means, monitoring a vibration amplitude of the treatment chamber; and
wherein the controlling means sets a frequency of the ultrasonic waves irradiated onto the to-be-treated liquid based on a monitoring result by the vibration amplitude monitoring means.

12. The production apparatus according to claim 8, further comprising a cooling means for performing the laser light illumination and the ultrasonic wave irradiation while cooling the to-be-treated liquid.

13. The production apparatus according to claim 8, wherein a dispersant is added to the to-be-treated liquid.

14. The production apparatus according to claim 8, wherein the substance is an organic compound.

* * * * *